United States Patent [19]

Porter et al.

[11] Patent Number: 4,725,441
[45] Date of Patent: Feb. 16, 1988

[54] MALTODEXTRIN COATING

[75] Inventors: Stuart C. Porter, Hatfield; Edward J. Woznicki, Douglassville, both of Pa.

[73] Assignee: Colorcon, Inc., West Point, Pa.

[21] Appl. No.: 914,056

[22] Filed: Oct. 1, 1986

Related U.S. Application Data

[62] Division of Ser. No. 633,954, Jul. 24, 1984.

[51] Int. Cl.$^4$ ............................ C08L 3/02; C08L 5/04
[52] U.S. Cl. ........................................ 424/479; 427/3; 106/210; 106/213; 106/214
[58] Field of Search ................ 536/103; 106/210, 213, 106/214; 424/35, 479; 427/3

[56] References Cited

U.S. PATENT DOCUMENTS

| | | | |
|---|---|---|---|
| 3,751,277 | 8/1973 | Small et al. .......................... | 514/778 |
| 3,873,694 | 3/1975 | Kanig .................................. | 424/154 |
| 4,533,562 | 8/1985 | Ikegami et al. ...................... | 427/3 |
| 4,596,602 | 6/1986 | Bennett .............................. | 536/103 |

*Primary Examiner*—Ronald W. Griffin
*Attorney, Agent, or Firm*—John F. A. Earley; John F. A. Earley, III

[57] ABSTRACT

A pharmaceutical, confectionery or food tablet coated on all its exterior surfaces with maltodextrin, which masks the characteristic taste of the tablet ingredients and does not have a slimy taste, with the coating composition comprising maltodextrin, an effective amount of a plasticizer to make the maltodextrin non-brittle and non-cracking when coated onto a tablet, an effective amount of a detackifier for making the maltodextrin and plasticizer non-tacky, a secondary film former to impart gloss and strength to the maltodextrin film coating, and a colorant for imparting color. A method of making tablets coated with maltodextrin.

13 Claims, No Drawings

MALTODEXTRIN COATING

This is a divisional of co-pending application Ser. No. 633,954, filed on July 24, 1984.

BACKGROUND OF THE INVENTION

1. Field of the Invention

This invention relates to the field of coating pharmaceutical, confectionery, and food tablets and the like including medicinal tablets, vitamin tablets, aspirin tablets, capsules, gum balls, and candy pieces.

2. Description of the Prior Art

Film coating of pharmaceutical, confectionery and food tablets with film coating polymers, such as hydroxypropyl methyl cellulose (HPMC), is known. Signorino U.S. Pat. No. 3,981,984 issued Sept. 21, 1976, discloses such coatings and is incorporated herein by reference together with the patents cited therein.

While HPMC and the other film coating polymers known in the art provide effective coatings, they are rather expensive, and have a somewhat disagreeable slimy taste.

SUMMARY OF THE INVENTION

It is an object of this invention to provide a coated pharmaceutical, confectionery and food tablet and the like which is effectively coated with a film coating other than the known film coating polymers such as HPMC.

It is another object to provide such a film coating which is less expensive and which eliminates disagreeable tastes such as a slimy taste.

The objects of the invention are accomplished by providing a coating of maltodextrin modified so that it is non-brittle and non-cracking and forms an effective coating.

The maltodextrin tablet coating of the invention shows enhanced color stability with water soluble dyes, as good as previous tablet coatings made with film forming polymers such as HPMC. Moreover, the maltodextrin tablet coating demonstrated a much greater color intensity than a HPMC system.

Normally, when pigment particles are added to a coating dispersion, the pigment particles weaken the film strength of the polymer film former such as HPMC. Surprisingly, adding pigment particles to the maltodextrin coating dispersion enhances the film strength of the maltodextrin and reduces cracking of a maltodextrin film coating. This is totally unexpected.

Tablet film coating experts have not recognized maltodextrin as a film coating because of its brittleness and tendency to crack.

As the art of tablet coating moved from sugar to film, the tablet coating lost some of its elegance and gloss. Film coated tablets do not have the high gloss of sugar coated tablets. However, with maltodextrin coated tablets, a high gloss is obtained, higher gloss than film coated tablets and matching that of sugar coated tablets.

The maltodextrin coating also shows high tint strength.

Color pigments are known to give superior color stability in polymer film formers such as HPMC, while soluble dyes give brighter color, but are less stable in HPMC. However, maltodextrin coatings with soluble dyes have brighter color and more stability than HPMC coatings with soluble dyes. This is unexpected, that maltodextrin soluble dye coatings are more brilliant and more stable than HPMC soluble dye coatings.

The weight gain of the tablet caused by the addition of the maltodextrin coating is about 0.5 to 2.0% on aspirin with 1% being preferred, about 3% on confection tablets, and about 3% on pharmaceutical tablets.

The viscosity of the maltodextrin coating suspension is very low, so although a coating dispersion of 15 parts solids in 85 parts water is preferred, a mixture of 25 to 30 parts solids to 70 to 75 parts water at room temperature is workable for spray coating, and solids loading of 50–60% is obtainable. If you heat the coating suspension, more solids may be added to the maltodextrin coating suspension, which is just the opposite with a HPMC coating suspension. An advantage of using hot maltodextrin coating suspensions is that the air temperature in the spray coating process may be kept below the air temperature required in spray coating with a HPMC coating suspension. This saves energy, and also makes it easier to coat gumballs which are sensitive to heat. Coating gumballs with HPMC coating suspensions may take 4 to 6 hours, while coating gumballs with maltodextrin coating suspensions may take 1 to 1.5 hours.

DETAILED DESCRIPTION

This invention is concerned with coating tablets, which are defined herein as pharmaceutical, confectionery and food tablets including medicinal tablets, vitamin tablets, aspirin tablets, capsules, chewing gum balls, pieces of candy and the like.

In accordance with the method invention, a coating mixture is made of maltodextrin which acts as a film former in the coating on the tablets, a plasticizer for making the coating non-brittle and non-cracking, and a detackifier for making the coating non-tacky. Other ingredients may include a secondary film former to give a high gloss and strength to the coating on the tablet, and color ingredients to give a desired color to the tablet coating.

The maltodextrin may be Maltrin maltodextrins made by Grain Processing Corp., Muscative, Iowa, or Amaizo Lo-Dex maltodextrins made by American Maize-Products Company, Hammond, Ind. By definition, maltodextrins (hydrolyzed cereal solids) are starch hydrolysates produced by converting pure refined corn starch into nutritive saccharides through the use of acids or specific enzymes. The carbohydrate composition is arranged to yield a DE (dextrose equivalent) of less than 20.

Maltodextrin by itself forms a film coating which is brittle and cracks, so that a tablet coated with maltodextrin is not protected from moisture which may penetrate the coating through the cracks. To prevent brittleness and cracking, a plasticizer is mixed in with the maltodextrin. Suitable plasticizers include hydrogenated glucose syrup (Lycasin by Roquette Corp., Gurnee, Ill.), polyethylene glycol 400, 3350, and 8000 (Carbowax made by Union Carbide), triacetin (triethylcitrate by Pfizer), Citoflex 2 (acetyltriethyl citrate by Pfizer), propylene glycol and glycerine. The plasticizers are used in a range of 3.5 to 15% by weight of the coating mixture, alone or in some combination, with 5 to 10% being preferred. Certain plasticizers cause considerable tackiness during tablet coating, but in combination with another plasticizer used as a detackifier, the tack is considerably reduced or eliminated.

Suitable detackifiers include polyethylene glycol 3350 and 8000, crystal gum (tapioca dextrin) and a modified derivatized starch, starch octenyl succinate, made by American Maize Products much like ARD 2326 except that it is made from standard corn starch instead of a waxy starch. The range of detackifiers is 2 to 20% by weight of the coating mixture with 10% being preferred.

The coating mixture may include a secondary film former to impart gloss and strength to the maltodextrin. Suitable secondary film formers are sodium alginate and propylene glycol alginate and they are used in a range of 3 to 15% by weight of the coating mixture, with 10% being preferred. The propylene glycol alginate may be a low viscosity Kelcoloid S, and the sodium alginate may be a higher viscosity Kelcoloid LVF, both made by the Kelco Division of Merck & Co. The Kelcoloid LVF may be about 5% by weight of the dry coating mixture without making it too viscous. The Kelcoloid S may be about 10% by weight of the dry coating mixture before the mixture becomes too viscous.

The film coating may or may not be pigmented. The addition of pigment particles adds strength to the maltodextrin film coatings. However, as the percentage of pigment particles increases, the gloss of the coated tablet decreases. Pigments are used in the range of 0 to 20% by weight of the mixture, and may include any U.S. Food and Drug Administration (FDA) approved FD & C aluminum lakes, D & C lakes and titanium dioxide. A list of such pigments appears in Signorino U.S. Pat. No. 3,981,984, which is incorporated herein by reference.

The coating may be colored by using FDA approved soluble dyes and titanium dioxide. The range of dye used is 0 to 2% by weight of the coating mixture, and the range of titanium dioxide is 0 to 10% by weight of the coating mixture.

All units and percentages used herein are by weight.

The following examples illustrate the invention as applied to film coating of pharmaceutical, food and confectionery, with gum balls being chosen as a specific example because of its sensitivity to high temperatures.

EXAMPLE 1

A coating mixture is made according to the following formula by mixing the ingredients in a blender until all the ingredients are evenly dispersed throughout the mixture.

| | |
|---|---|
| 69.5 g | maltodextrin (Maltrin M150 by Grain Processing Corp.) |
| 3.0 g | polyethylene glycol 400 |
| 5.0 g | polyethylene glycol 3350 |
| 3.0 g | glycerine |
| 10.0 g | propylene glycol alginate (Kelcoloid S) |
| 8.0 g | titanium dioxide |
| 1.5 g | FD&C yellow #5 aluminum lake |
| 100.0 g | |

The maltodextrin is the film former, the polyethylene glycol 400 and the glycerine are the plasticizers, the polyethylene glycol 3350 is the detackifier, the propylene glycol alginate is the secondary film former, the titanium dioxide is an opacifier, and the FD & C yellow #5 gives the coating a yellow color.

The maltodextrin is non-toxic, edible and is in powdered form and is mixed in with the other ingredients in the formula.

A spraying suspension is made by suspending 15 parts by weight of the coating mixture in 85 parts by weight of water with suitable agitation to disperse the mixture in the suspension.

3.8 kg of ¾ inch gum balls are placed in a 24 inch conventional coating pan which is rotated at 22 rpm. The spraying suspension is sprayed onto the gum balls by a 460 Binks air gun, with a 7016 Masterflex peristaltic pump, at 40 psi atomizing pressure delivered at a rate of 15 grams per minute. The drying air is at 45° C., and the coating suspension is heated to 70° C., application time is 15 minutes and 115 grams total of film is applied to the gum balls.

The maltodextrin 150 used is made by Grain Processing Corporation, Muscatine, Iowa, and it is used as a film former. The maltodextrin without other ingredients produces a film coating on a tablet which is brittle and cracks. To overcome this brittleness and cracking, the polyethylene glycol 400 and the glycerine are provided as plasticizers. However, this makes the coating sticky so to overcome this stickiness, polyethylene glycol 3350 is provided as a detackifier. The propylene glycol alginate acts as a secondary film former to give the coating a desired gloss. The titanium dioxide and FD & C yellow No. 5 aluminum lake are provided as color ingredients, with the titanium dioxide acting as an opacifier and the yellow lake providing a yellow color to the coating.

EXAMPLE 2

A coating mixture is made up as in Example 1 but having the following formula with 1.0 g of FD & C yellow dye being substituted for the 1.0 g of FD & C yellow No. 5 aluminum lake.

| | |
|---|---|
| 69.5 g | maltodextrin (Maltrin M150) |
| 3.0 g | polyethylene glycol 400 |
| 5.0 g | polyethylene glycol 3350 |
| 3.0 g | glycerine |
| 10.0 g | propylene glycol alginate (Kelcoloid S) |
| 8.5 g | titanium dioxide |
| 1.0 g | FD&C yellow No. 5 dye |
| 100.0 g | |

The ingredients are mixed and a coating suspension is prepared as in Example 1, and the gum balls are spray coated as in Example 1.

EXAMPLE 3

A coating mixture is made up as in Example 1 but having the following formula.

| | |
|---|---|
| 70.0 g | maltodextrin (Maltrin M150) |
| 3.5 g | polyethylene glycol 400 |
| 3.5 g | polyethylene glycol 3350 |
| 3.0 g | sodium alginate (Kelcoloid LVF) |
| 10.0 g | titanium dioxide |
| 10.0 g | FD&C yellow No. 6 aluminum lake |
| 100.0 g | |

The ingredients are mixed and a coating suspension is prepared as in Example 1, and the gum balls are spray coated as in Example 1.

EXAMPLE 4

A coating mixture is made up as in Example 1 but having the following formula.

| | |
|---|---|
| 65.0 g | maltodextrin (Maltrin M150) |

|                                                        |
| ------------------------------------------------------ |
| 10.0 g polyethylene glycol 400                         |
| 5.0 g polyethylene glycol 3350                         |
| 15.0 g propylene glycol alginate (Kelcoloid S)         |
| 5.0 g titanium dioxide                                 |
| 100.0 g                                                |

The ingredients are mixed and a coating suspension is prepared as in Example 1, and the gum balls are spray coated as in Example 1.

EXAMPLE 5

A coating mixture is made up as in Example 1 but having the following formula.

|                                                        |
| ------------------------------------------------------ |
| 69.0 g maltodextrin (Maltrin M150)                     |
| 3.5 g polyethylene glycol 400                          |
| 3.5 g polyethylene glycol 3350                         |
| 4.0 g sodium alginate (Kelcoloid LVF)                  |
| 10.0 g titanium dioxide                                |
| 10.0 g FD&C No. 3 aluminum lake                        |
| 100.0 g                                                |

The ingredients are mixed and a coating suspension is prepared as in Example 1, and the gum balls are spray coated as in Example 1.

EXAMPLE 6

A coating mixture is made up as in Example 1 but having the following formula.

|                                                        |
| ------------------------------------------------------ |
| 60.0 g maltodextrin (Maltrin M150)                     |
| 15.0 g polyethylene glycol 400                         |
| 5.0 g polyethylene glycol 3350                         |
| 5.0 g sodium alginate (Kelcoloid LVF)                  |
| 15.0 g titanium dioxide                                |
| 100.0 g                                                |

The coating ingredients are mixed and a coating suspension is prepared as in Example 1, and the gum balls are spray coated as in Example 1.

EXAMPLE 7

A coating mixture is made up as in Example 1 but having the following formula.

|                                                        |
| ------------------------------------------------------ |
| 75.0 g maltodextrin (Maltrin M150)                     |
| 10.0 g polyethylene glycol 400                         |
| 5.0 g polyethylene glycol 3350                         |
| 10.0 g propylene glycol alginate (Kelcoloid S)         |
| 100.0 g                                                |

The ingredients are mixed and a coating suspension is prepared as in Example 1, and the gum balls are spray coated as in Example 1.

Other formulations of coating mixtures which are made into a coating suspension or solution, and which are spray coated onto tablets, are as follows:

EXAMPLE 8

|                                                        |
| ------------------------------------------------------ |
| 73.0 g maltodextrin (Lo-Dex 5 by American Maize)       |
| 5.0 g hydrogenated glucose syrup (Lycasin)             |
| 5.0 g polyethylene glycol 400                          |
| 10.0 g propylene glycol alginate                       |
| 6.0 g titanium dioxide                                 |
| 1.0 g FD&C yellow #6 dye                               |

|          |
| -------- |
| 100.0 g  |

EXAMPLE 9

|                                                        |
| ------------------------------------------------------ |
| 68.0 g maltodextrin (Lo-Dex 5)                         |
| 10.0 g hydrogenated glucose syrup (Lycasin)            |
| 5.0 g polyethylene glycol 400                          |
| 10.0 g propylene glycol alginate                       |
| 6.0 g titanium dioxide                                 |
| 1.0 g FD&C yellow #6 dye                               |
| 100.0 g                                                |

EXAMPLE 10

|                                                        |
| ------------------------------------------------------ |
| 68.0 g maltodextrin (Lo-Dex 5)                         |
| 5.0 g hydrogenated glucose syrup (Lycasin)             |
| 10.0 g polyethylene glycol 400                         |
| 10.0 g propylene glycol alginate                       |
| 6.0 g titanium dioxide                                 |
| 1.0 g FD&C yellow #6 dye                               |
| 100.0 g                                                |

EXAMPLE 11

|                                                        |
| ------------------------------------------------------ |
| 75.0 g maltodextrin (Maltrin M150 by Grain Processing Corp.) |
| 13.0 g polyethylene glycol 400                         |
| 2.0 g polyethylene glycol 3350                         |
| 10.0 g sodium alginate                                 |
| 100.0 g                                                |

EXAMPLE 12

|                                                        |
| ------------------------------------------------------ |
| 69.5 g maltodextrin (Maltrin M150)                     |
| 3.0 g polyethylene glycol 400                          |
| 5.0 g polyethylene glycol 3350                         |
| 3.0 g glycerine                                        |
| 10.0 g propylene glycol alginate                       |
| 7.5 g titanium dioxide                                 |
| 2.0 g FD&C yellow #5 dye                               |
| 100.0 g                                                |

Conventional film forming polymeric spray coating suspensions, like those made with HPMC, thicken and gel at high temperatures. In contrast to this, it has been found that the herein described maltodextrin coating suspensions become less viscous at high temperatures, which is an advantage in spray coating suspensions having a high solids content. Also, since the maltodextrin coating suspensions can be heated they can be sprayed on heat sensitive materials, like gum balls, without using excessively hot drying air that would harm the gum balls. In other words, the heated maltodextrin coating suspension does not harm the gum balls, whereas the heated drying air would. For example, the maltodextrin coating suspensions have been successfully sprayed onto tablets at temperatures of 80° C. with the drying air at 30° C. Also, the maltodextrin coating suspensions have been successfully sprayed onto tablets at room temperature with the drying air at 80° C. Tablets may be successfully sprayed by the maltodextrin coating suspensions at all temperatures within those ranges.

Maltodextrin coating suspensions are used to coat aspirin tablets which are easily-swallowed, powder-free, gastric disintegrable, thinly-coated, and which do not have the characteristic aspirin taste, do not produce the esophageal discomfort of an uncoated aspirin tablet, and which disintegrate in the stomach not much slower than an uncoated aspirin tablet. The method of coating aspirin tablets comprises aqueous spray-coating maltodextrin onto all exterior surfaces of the aspirin tablets, with the maltodextrin being 0.5 to 2.0 parts by weight per 100 parts by weight of the uncoated aspirin tablet.

In one embodiment of the method, an aqueous coating solution is made of 2% to 15% by weight of a coating mixture of the maltodextrin 60–70%, plasticizer about 10%, detackifier about 10–20%, and secondary film former about 10%, with 85–98% water, and this coating solution is sprayed onto uncoated aspirin tablets in a conventional coating pan in a chamber with the inlet and outlet air rates and temperature being effective to rapidly evaporate the water and to apply a thin coating of maltodextrin onto the tablets without causing them to decompose or disintegrate.

The coated aspirin tablet of this invention comprises an easily-swallowed, powder-free and gastric-disintegrable aspirin tablet thinly coated on all exterior surfaces with maltodextrin, with the coating being thin enough not to change significantly the rate of disintegration in the stomach. The coating masks the characteristic taste of aspirin, and smooths the ingestion of the aspirin tablet through the esophogus. In a preferred embodiment the aspirin tablet is uniformly covered with a coating of maltodextrin 60–70%, plasticizer about 10%, detackifier about 10–20%, and secondary film former about 10%.

The following examples illustrate the coated aspirin embodiment of the invention.

EXAMPLE 13

A dry coating mixture is made up as in Example 1 but having the following formula.

| | |
|---|---|
| 70 g | maltodextrin (Maltrin M150) |
| 10 g | polyethylene glycol 400 |
| 10 g | modified derivatized starch |
| 10 g | propylene glycol alginate (Kelcoloid S) |
| 100 g | |

A coating solution is prepared by suspending 15 parts by weight of the mixture in 85 parts of water by agitation, and aspirin tablets are spray coated as in Example 1.

The maltodextrin 150 is made by Grain Processing Corporation, Muscatine, Iowa, the modified derivatized starch is made by American Maize Products, Hammond, Ind., the polyethylene glycol 400 is Carbowax by Union Carbide, and the propylene glycol alginate is Kelcoloid S by the Kelco Division of Merck & Company.

EXAMPLE 14

The method of Example 13, except the coating solution is prepared by suspending 2 parts by weight of the mixture into 98 parts of water.

EXAMPLE 15

A coating mixture is made as in Example 1 having the following formula.

| | |
|---|---|
| 60.0 g | maltodextrin (Maltrin M150) |
| 10.0 g | polyethylene glycol 400 |
| 20.0 g | modified derivatized starch |
| 10.0 g | propylene glycol alginate (Kelcoloid S) |
| 100.0 g | |

A coating solution is made as in Example 13 and aspirin tablets are spray coated as in Example 13.

EXAMPLE 16

A coating mixture is made as in Example 1 having the following formula.

| | |
|---|---|
| 70.0 g | maltodextrin (Maltrin M150) |
| 10.0 g | polyethylene glycol 400 |
| 10.0 g | crystal gum (tapioca dextrin) |
| 10.0 g | propylene glycol alginate (Kelcoloid S) |
| 100.0 g | |

A coating solution is made as in Example 13 and aspirin tablets are spray coated as in Example 13.

EXAMPLE 17

A coating mixture is made as in Example 1 having the following formula.

| | |
|---|---|
| 60.0 g | maltodextrin (Maltrin M150) |
| 10.0 g | propylene glycol 400 |
| 20.0 g | crystal gum (tapioca dextrin) |
| 10.0 g | propylene glycol alginate (Kelcoloid S) |
| 100.0 g | |

A coating solution is made as in Example 15 and aspirin tablets are spray coated as in Example 15.

We claim:

1. A dry powder edible film coating composition for use in pharmaceuticals, confectionery and food, comprising a dry mixture obtained by dry blending ingredients, including
   - a primary film-former consisting essentially of powdered particles of film forming non-toxic edible maltodextrin,
   - an effective amount of a plasticizer for making the maltodextrin non-brittle and non-cracking when coated onto a tablet, and
   - an effective amount of a detackifier for making the maltodextrin and plasticizer non-sticky or non-tacky.

2. The film-coating composition of claim 1, including
   an effective amount of a secondary film former to impart gloss and strength to the maltodextrin film coating.

3. The film coating composition of claim 1, including
   a colorant for imparting color to the maltodextrin film coating.

4. The film coating composition of claim 3,
   said colorant being titanium dioxide, FD & C lakes, or D & C lakes.

5. The film coating composition of claim 3,
   said colorant being titanium dioxide and a soluble dye.

6. The film coating composition of claim 1,
   said plasticizer being 3.5% to 15% by weight of the coating mixture.

7. The film coating composition of claim 1, the plasticizer being hydrogenated glucose syrup, polyethylene glycol 400, 3350, or 8000, triacetin, acetyltriethyl citrate, propylene glycol or glycerin.

8. The film coating composition of claim 1, the detackifier being 2 to 20% by weight of the coating mixture.

9. The film coating composition of claim 1, the detackifier being modified derivatized starch, tapicoa dextrin, polyethylene glycol 3350 or 8000.

10. The film coating composition of claim 2, the secondary film former being propylene glycol alginate or sodium alginate.

11. The film coating composition of claim 2, the secondary film former being in a range of 3 to 15% by weight of the coating mixture.

12. The film coating composition of claim 1, including a colorant for imparting color to the maltodextrin,
said colorant being soluble dyes and titanium dioxide,
said dyes being in a range of 0 to 2% by weight of the coating,
and the titanium dioxide being in a range of 0 to 10% by weight of the coating composition.

13. A dry powder edible film coating composition for use in pharmaceuticals, confectionery and food, comprising a dry mixture obtained by blending ingredients, including
a primary film-former consisting essentially of powdered particles of film forming non-toxic edible maltodextrin,
an effective amount of a plasticizer for making the maltodextrin non-brittle and non-cracking when coated onto a tablet,
an effective amount of a detackifier for making the maltodextrin and plasticizer non-sticky and non-tacky,
an effective amount of a secondary film former to impart gloss and strength to the maltodextrin film coating,
a colorant for imparting color to the maltodextrin film coating,
the plasticizer being about 3.5% to 15% by weight of the coating mixture,
the plasticizer being hydrogenated glucose syrup, polyethylene glycol 400, 3350, or 8000, triacetin, acetyltriethyl citrate, propylene glycol or glycerine,
the detackifier being 2 to 20% by weight of the coating mixture,
the detackifier being modified derivitized starch, tapioca dextrin, polyethylene glycol 3350 or 8000,
the secondary film former being propylene glycol alignate or sodium alginate,
the secondary film former being in a range of 3 to 15% by weight of the coating mixture,
said colorant being titanium dioxide, FD & C lakes, D & C lakes, or soluble dyes and titanium dioxide,
said color ingredients being in the range of 0 to 20% of the weight of the solids content of the coating composition.

* * * * *